(12) United States Patent
Gonzalez et al.

(10) Patent No.: US 6,433,169 B1
(45) Date of Patent: Aug. 13, 2002

(54) PROCESS FOR THE PREPARATION OF 2-ALKOXY-6-TRIFLUOROMETHYL-N-([1,2,4]TRIAZOLO[1,5-C]PYRIMIDIN-2-YL)BENZENESULFONAMIDES

(75) Inventors: Michael Allen Gonzalez, Sanford; Eric Wayne Otterbacher, Midland, both of MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/961,617

(22) Filed: Sep. 24, 2001

Related U.S. Application Data

(60) Provisional application No. 60/235,442, filed on Sep. 26, 2000.

(51) Int. Cl.[7] .............................................. C07D 487/04
(52) U.S. Cl. ...................................................... 544/263
(58) Field of Search .......................................... 544/263

(56) References Cited

U.S. PATENT DOCUMENTS 5,858,924 A    1/1999    Johnson et al. ............. 504/241

*Primary Examiner*—Mark L. Berch
(74) *Attorney, Agent, or Firm*—Craig E. Mixan

(57) ABSTRACT

2-Alkoxy-6-trifluoromethyl-N-([1,2,4]triazolo[1,5-c]pyrimidin-2-yl)benzenesulfonamides are prepared by introducing the 2-alkoxy substituent of the benzenesulfonamide ring in the last step by contacting the corresponding 2-fluoro substituted material with the appropriate alkoxide.

6 Claims, No Drawings

PROCESS FOR THE PREPARATION OF 2-ALKOXY-6-TRIFLUOROMETHYL-N-([1,2,4] TRIAZOLO[1,5-C]PYRIMIDIN-2-YL) BENZENESULFONAMIDES

This application claims priority from U.S. Provisional Application Ser. No. 60/235,442, filed Sep. 26, 2000.

BACKGROUND OF THE INVENTION

The present invention concerns a process for the preparation of 2-alkoxy-6-trifluoromethyl-N-([1,2,4]triazolo[1,5-c]pyrimidin-2-yl) benzenesulfonamides. More particularly, the present invention concerns the preparation of these compounds in which the 2-alkoxy substituent of the benzenesulfonamide ring is introduced in the last step by contacting the corresponding 2-fluoro substituted material with the appropriate alkoxide.

U.S. Pat. No. 5,858,924 describes certain substituted benzenesulfonamide compounds and their use as herbicides. Among the disclosed herbicides, the 2-alkoxy-6-trifluoromethyl-N-([1,2,4]triazolo[1,5-c]pyrimidin-2-yl) benzenesulfonamides are particularly useful. Normally these materials are prepared by condensing the appropriately substituted 2-amino[1,2,4]triazolo-[1,5-c]pyrimidine with the appropriately substituted benzenesulfonyl chloride.

It would be advantageous to have an alternative process to produce these materials. It would be particularly advantageous to have a process in which the 2-alkoxy substituent of the benzenesulfonamide ring is added late in the process, especially when the alkoxy substituent is substituted with fluorine atoms and its introduction requires one of the more expensive starting materials employed in the overall manufacturing scheme.

SUMMARY OF THE INVENTION

The present invention concerns a process for the preparation of a 2-alkoxy-6-trifluoromethyl-N-([1,2,4]triazolo[1,5-c]pyrimidin-2-yl) benzenesulfonamide of Formula I

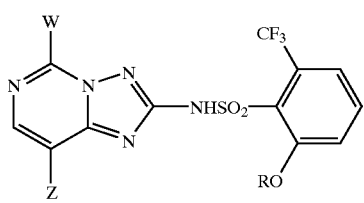

wherein
W represents H or O($C_1$–$C_3$ alkyl);
Z represents H or O($C_1$–$C_3$ alkyl), with the proviso that at least one of W or Z represents O($C_1$–$C_3$ alkyl); and
R represents $C_1$–$C_4$ alkyl optionally substituted with at least 2 and up to the maximum possible number of fluorine atoms which comprises contacting a 2-fluoro-6-trifluoromethyl-N-([1,2,4]triazolo-[1,5-c]pyrimidin-2-yl)benzenesulfonamide of Formula II

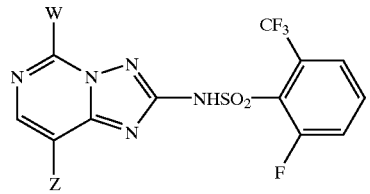

wherein
W and Z are as previously defined
with an alcohol ROH wherein R is as previously defined and at least 2 molar equivalents of base in a polar aprotic organic solvent.

DETAILED DESCRIPTION OF THE INVENTION

The term alkyl and derivative terms such as alkoxy and alcohol, as used herein, include straight chain, branched chain and cyclic groups. Thus, typical alkyl groups are methyl, ethyl, 1-methylethyl, propyl, cyclopropyl, butyl, 1,1-dimethylethyl, cyclobutyl and 1-methylpropyl. Methyl and ethyl are often preferred. Alkyl groups are sometimes referred to as normal (n), iso (i), secondary (s) or tertiary (t). Typical alkyls optionally substituted with at least 2 and up to the maximum possible number of fluorine atoms include trifluoromethyl, 2,2,2-tri-fluoroethyl, 2,2-difluoroethyl and 2,2,3,3,3-pentafluoropropyl.

The 2-fluoro-6-trifluoromethyl-N-([1,2,4]triazolo[1,5-c]pyrimidin-2-yl)benzenesulfonamide starting materials are described in U.S. Pat. No. 5,858,924 and can be prepared by condensing the appropriately substituted 2-amino[1,2,4]triazolo[1,5-c]pyrimidine with 2-fluoro-6-trifluoromethylbenzenesulfonyl chloride. The 2-fluoro-6-trifluoromethylbenzenesulfonyl chloride can be prepared, for example, from 2-fluoro-6-trifluoromethylaniline by diazotization followed by treatment with sulfur dioxide and cupric chloride.

The conversion of the 2-fluorobenzenesulfonamide to the corresponding 2-alkoxybenzenesulfonamide is accomplished by contacting the 2-fluorobenzenesulfonamide with the appropriate alcohol and at least 2 equivalents of base in a polar aprotic solvent.

Although higher alcohols can be used in the present process, since the more herbicidally effective 2-alkoxy-6-trifluoromethyl-N-([1,2,4]triazolo-[1,5-c]pyrimidin-2-yl) benzenesulfonamides contain $C_1$–$C_4$ alkoxy groups, the preferred alcohols are the corresponding $C_1$–$C_4$ alcohols. The most preferred alcohols are those substituted with at least 2 and up to the maximum possible number of fluorine atoms. While only a stoichiometric amount of alcohol is required to achieve complete conversion, oftentimes it is beneficial to employ an excess of the alcohol. Because of the relative convenience with which the alcohol can be recovered and recycled, for example, by distillation, two- to three-fold or more molar excesses of the alcohol can be employed. A further benefit to having excess alcohol is increased yield, purity, and reduced cycle time.

Since it is necessary to convert at least one equivalent of the alcohol to the corresponding alkoxide and since another equivalent of base is consumed in neutralizing the relatively acidic sulfonamide proton, at least two equivalents of base based on the amount of sulfonamide are required. An additional excess of base is often preferred. Any base or mixture of bases which is sufficiently strong to convert the alcohol to the alkoxide is suitable, as long as it does not cause degradation to the starting materials or product. Sodium hydroxide, potassium hydroxide, sodium hydride, potassium hydride and potassium t-butoxide are examples of acceptable bases with potassium t-butoxide and sodium hydride being preferred.

Polar aprotic organic solvents are employed as the reaction medium in the present process. Suitable polar aprotic organic solvents include alkyl nitrites such as acetonitrile, ethers such as tetrahydrofuran, 1,4-dioxane and 1,2-dimethoxyethane, carboxylic esters such as ethyl acetate, carboxylic amides such as dimethyl formamide, dimethyl acetamide and N-methyl pyrrolidinone, ureas such as 1,3-dimethyl-2-imidazolidinone or mixtures thereof.

The reaction is conducted at a temperature from about −10° C. to about 40° C. The optimal temperature can be readily determined by routine optimization. The preferred temperature is from about 10° C. to about 30° C.

The pressure under which the process is performed is not critical and the process is usually carried out at or slightly above atmospheric pressure. The process is preferably conducted under a dry inert atmosphere such as that provided by a nitrogen blanket.

The final product can be isolated and recovered by conventional procedures well known to those skilled in the art. Typically, the reaction mixture is diluted with water and the precipitated product is collected by filtration and dried.

In a typical reaction, the 2-fluoro-6-trifluoromethyl-N-([1,2,4]-triazolo[1,5-c]pyrimidin-2-yl)benzenesulfonamide starting material is at least partially dissolved in the polar aprotic organic solvent and treated with about 2–3 equivalents of base and 2–3 equivalents of alcohol at 10–30° C. for about 15–30 hours. After the reaction is complete, the reaction mixture is diluted with water and the precipitated product is collected by filtration and dried.

The following examples are presented to illustrate the invention.

EXAMPLES

1. Preparation of 2-Fluoro-6-trifluoromethylbenzenesulfonyl Chloride

To a mechanically stirred mixture of 2-fluoro-6-trifluoromethylaniline (10.0 g, 55.8 mmol) in concentrated hydrochloric acid (20 mL) and glacial acetic acid (6 mL) was added a solution of sodium nitrite (4.25 g, 61.4 mmol) in water (6 mL) dropwise at −10° C. The resulting orange/white suspension was stirred at −10° C. for 30 minutes, then added in portions to a solution of cuprous chloride (1.7 g, 16.7 mmol) and sulfur dioxide (about 20 g, 312 mmol) in glacial acetic acid (60 mL) at 0° C. A mild exotherm and vigorous gas evolution were observed after each addition. The resulting dark green mixture was warmed to room temperature and stirred for 25 minutes (min). The reaction was poured into ice water (600 mL) and extracted with diethyl ether. The organics were combined, washed with aqueous sodium bicarbonate, dried ($MgSO_4$), filtered, and the solvent removed in vacuo to afford the crude product as a dark oil (8.45 g, 15 58% yield).

$^1$H NMR ($CDCl_3$): δ7.57 (m, 1 H), 7.75 (d, 1H, J=8.0 Hz.), 7.84 (m, 1H).

2. Preparation of 2-Fluoro-6-trifluoromethyl-N-(5,8-dimethoxy-1,2,4triazolo[1,5-c]pyrimidin-2-yl)benzenesulfonamide 2-Amino-5,8-dimethoxy(1,2,4)triazolo[1,5-c]pyrimidine (1.0 g, 5.1 mmol) was suspended in 15 mL of dry acetonitrile in a round bottom flask equipped with magnetic stirring. To this suspension was added crude 2-fluoro-6-trifluoromethylbenzenesulfonyl chloride (3.16 g, 10.2 mmol), dry pyridine (0.8 g, 10.2 mmol), dry dimethylsulfoxide (DMSO, 0.1 g, 1.3 mmol), and the flask was fitted with a $CaSO_4$ drying tube. The reaction was monitored by HPLC analysis over a 9 day period, during which time an additional 4 equivalents of pyridine and 0.1 equivalents of DMSO were added. The dark solution was diluted with methylene chloride (300 mL), washed with 2N hydrochloric acid (2×200 mL), washed with water (2×200 mL), dried ($MgSO_4$), filtered, and the solvent evaporated in vacuo to give a brown residue. The brown residue was triturated 5 with diethyl ether to afford the product as a tan solid: (1.0 g, 46% yield), mp 201–203° C.; Anal. Calcd for $C_{14}H_{11}F_4N_5O_4S$: C 39.91, H 2.63, N 16.62, S 7.61; found: C 39.77, H 2.46, N 16.34, S 7.64. $^1$H NMR (DMSO-$d_6$): δ 3.85 (s, 3H), 4.05 (s, 3H), 7.58 (s, 1H), 7.73 (m, 1H), 7.88 (s, 2H), 12.85 (bs, 1H).

3. Preparation of 2-(2,2-Difluoroethoxy)-6-trifluoromethyl-N-(5, 8-dimethoxy[1,2,4]triazolo[1, 5-c]pyrimidin-2-yl)benzenesulfonamide Sodium hydride (1.21 g, 30 mmol, as a 60% suspension in mineral oil) was charged into a round bottom flask equipped with magnetic stirring and a nitrogen blanket, washed twice with 10 mL hexanes, dried of residual hexanes under a nitrogen stream, and suspended in 1,2-dimethoxyethane (20 mL). After cooling in an ice bath to about 10° C., 2-fluoro-6-trifluoromethyl-N-(5, 8-dimethoxy[ 1,2,4]triazolo[1,5-c]pyrimidin-2-yl) benzenesulfonamide (4.21 g, about 98.5% purity, 10 mmol) was added over about 5 min, rinsing in with 1 mL 1,2-dimethoxyethane. A slight exotherm to about 13° C. occurred. Continued ice bath cooling lowered temperature to about 6° C. over about 10 min. To the off-white suspension was added 2,2-difluoroethanol (0.815 niL, 13 mmol) over about 5 min. A slight exotherm to about 13° C. occurred. The light tan suspension was stirred at about 5–10° C. for about 1 hr, then the ice bath was removed. The temperature peaked at about 28° C. (about 2° C. above room temperature) about 0.5 hr later. The tan suspension was stirred overnight (about 20 hr total reaction time), then worked up by addition of the reaction mixture over about 7 min into 5% hydrochloric acid (80 mL, 112 mmol) at about 5–10° C. with ice bath cooling. The suspension was stirred about 18 min at about 9° C., then filtered, washed twice with 15 mL water each, washed twice with 15 mL methanol each, air-dried for about 2 hr, and finally vacuum-dried at about 0.02 mm Hg for about 2 hr over phosphorus pentoxide to afford the product as a white powder (4.34 g, about 92.8% purity, 8.3 mmol, about 83% yield).

4. Preparation of 2-(2.2-Difluoroethoxv)-6-trifluorometh 1-N-(5,8-dimethoxy[1,2,4]triazolo[1,5-c]pyrimidin-2-yl)benzenesulfonamide 2-Fluoro-6-trifluoromethyl-N-(5,8-dimethoxy[1,2,4] triazolo[1,5-c]-pyrimidin-2-yl)benzenesulfonamide (33.71 g, about 94.1% purity, 75 mmol) and 1,4-dioxane (345.21 g) were charged into a round bottom flask equipped with mechanical stirring, a nitrogen blanket, a Vigreux distillation column, an overheads condenser, and a graduated overheads receiver. The reaction mixture was dried by distillation, taking 94.02 g overhead at up to 101° C. overheads temperature. The reaction mixture was allowed to cool to about room temperature (about 24° C.) over about 2 hr, then 2,2-difluoroethanol (21.38 g, 260 mmol, dried over 3Å molecular sieves) was added via syringe. The reaction mixture was cooled to about 16° C. using a cool water bath.

In a separate flask, sodium hydride (8.02 g, 200 mmol, as a 60% suspension in mineral oil) was washed twice with 30 mL hexanes, dried of residual hexanes under a nitrogen stream, and suspended in 1,4-dioxane (58 mL). The sodium hydride suspension in 1,4-dioxane was added via cannula to the dried 2-fluoro-6-trifluoromethyl-N-(5,8-dimethoxy[1,2,4]triazolo[1,5-c]pyrimidin-2-yl)-benzenesulfonamide, 2,2-difluoroethanol, and 1,4-dioxane reaction mixture over about 9 min at about 16–26° C. with cool water/ice bath cooling. The cooling bath was removed, the reaction mixture was stirred at room temperature for about 24 hr, and then worked up by addition of the reaction mixture over about 0.5 hr into 5% hydrochloric acid (1403 mL, 1970 mmol) at about 4–7° C. with ice bath cooling. The suspension was stirred about 14 min at about 5° C., then filtered, washed twice with 134 mL water each, washed once with 134 mL methanol, air-dried overnight (about 15 hr) to afford the product as an off-white powder (38.31 g, about 87.7% purity including about 4.1% loss on drying, about 69 mmol, about 92% yield).

What is claimed is:

1. A process for the preparation of a 2-alkoxy-6-trifluoromethyl-N-([1,2,4]triazolo[1,5-c]pyrimidin-2-yl)benzenesulfonamide of Formula I

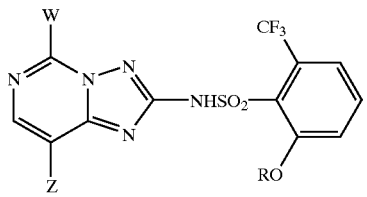

wherein

W represents H or O($C_1$–$C_3$ alkyl);

Z represents H or O($C_1$–$C_3$ alkyl), with the proviso that at least one of W or Z represents O($C_1$–$C_3$ alkyl); and R represents $C_1$–$C_4$ alkyl optionally substituted with at least 2 and up to the maximum possible number of fluorine atoms which comprises contacting a 2-fluoro-6-trifluoromethyl-N-([1,2,4]triazolo-[1,5-c]pyrimidin-2-yl)benzenesulfonamide of Formula II

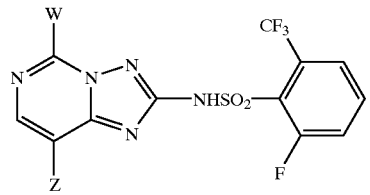

wherein

W and Z are as previously defined with an alcohol ROH wherein R is as previously defined and at least 2 molar equivalents of base in a polar aprotic organic solvent.

2. The process of claim 1 in which the polar aprotic organic solvent is an alkyl nitrile, an ether, a carboxylic ester, a carboxylic amide, a urea or mixtures thereof.

3. The process of claim 1 in which the process is conducted at a temperature from about −10 to about 40° C.

4. The process of claim 1 in which W and Z are both $OCH_3$.

5. The process of claim 1 in which R is −$CF_2CH_3$.

6. The process of claim 1 in which the base is sodium hydride. or potassium t-butoxide.

\* \* \* \* \*